(12) United States Patent
Jackson

(10) Patent No.: US 10,918,512 B2
(45) Date of Patent: Feb. 16, 2021

(54) GIRD COMPRESSION TENSIONING GARMENT WITH CERVICAL COLLAR

(71) Applicant: James Earl Jackson, Bronx, NY (US)

(72) Inventor: James Earl Jackson, Bronx, NY (US)

(73) Assignee: James Earl Jackson, Bronx, NY (US)

( * ) Notice: Subject to any disclaimer, the term of this patent is extended or adjusted under 35 U.S.C. 154(b) by 617 days.

(21) Appl. No.: 15/370,619

(22) Filed: Dec. 6, 2016

(65) Prior Publication Data

US 2018/0153726 A1    Jun. 7, 2018

(51) Int. Cl.
*A61F 5/02* (2006.01)
*A61F 5/055* (2006.01)
*A41D 1/04* (2006.01)

(52) U.S. Cl.
CPC .................. *A61F 5/02* (2013.01); *A41D 1/04* (2013.01); *A61F 5/055* (2013.01); *A41D 2300/32* (2013.01)

(58) Field of Classification Search
CPC .. A61F 5/02; A61F 13/14; A61F 5/028; A61F 5/055; A41D 13/0531; A41D 2400/32; A41D 2400/38; A41D 1/23; A41D 2300/32; A41D 13/0512; A61H 2201/1623; A61H 2201/1645; A41B 1/08; A41B 1/18
USPC ..... 602/12, 18, 19; 2/44, 300, 122, 467, 468
See application file for complete search history.

(56) References Cited

U.S. PATENT DOCUMENTS

| | | | |
|---|---|---|---|
| 5,007,412 A * | 4/1991 | DeWall | A41D 13/0531 128/DIG. 15 |
| 5,074,292 A | 12/1991 | Cox | |
| 5,810,699 A | 9/1998 | Nadeau | |
| 6,067,665 A | 5/2000 | DePalma et al. | |
| 6,195,802 B1 | 3/2001 | Armellino | |
| 6,748,601 B2 | 6/2004 | LaShoto et al. | |
| D627,135 S | 11/2010 | Turner | |
| 8,397,316 B2 | 3/2013 | Rosen et al. | |
| 9,226,534 B2 | 1/2016 | Puni | |
| 2012/0022418 A1 | 1/2012 | Gamboa et al. | |
| 2012/0122370 A1 * | 5/2012 | Heath | A41C 3/0057 450/80 |
| 2014/0303532 A1 * | 10/2014 | Harding | A41B 3/02 601/84 |
| 2016/0029702 A1 * | 2/2016 | Griffin | A41B 1/08 2/116 |
| 2019/0125326 A1 * | 5/2019 | Galbierz | A61B 17/02 |

OTHER PUBLICATIONS

The Brace Shop, DonJoy Sully Shoulder Brace. Printed Oct. 31, 2016. https://www.braceshop.com/product/don-joy-sully-shoulder-stabilizer.
HK Surgical Maximum Male Compression Vest. Printed Nov. 4, 2016. https://www.hksurgical.com/product/male-compression-vest.html.

\* cited by examiner

*Primary Examiner* — Ophelia A Hawthorne
*Assistant Examiner* — Caitlin A Carreiro
(74) *Attorney, Agent, or Firm* — Edward L. Tulin

(57) ABSTRACT

A gird compression garment designed to provide compressive support extending throughout the cervical and thoracic portions of the wearer's spine so as to help relieve pain and to help promote healing from muscular/skeletal ailments and injuries. This gird compression garment is constructed of a resiliently flexible and stretchable material and includes a cervical collar that extends to the base of the skull of a wearer and a fastening device adapted to vary the amount of compressive force exerted by the garment.

14 Claims, 4 Drawing Sheets

GIRD COMPRESSION TENSIONING GARMENT WITH CERVICAL COLLAR

BACKGROUND OF THE INVENTION

The present invention generally relates to a compression garment that, through its unique combination of elements, is adapted to provide gird compressive support for both the cervical and thoracic portions of a wearer's body.

Millions of individuals suffer from chronic neck, shoulder, and upper back pain. There are a litany of causes for such chronic pain, including injuries, muscle strain, joint damage, radiculopathy, and complications from surgeries such as those affecting the upper spine.

The spine consists of thirty-three vertebrae that have been categorized into five regions: the cervical, thoracic, lumbar, sacrum, and coccyx regions. The cervical region consists of 7 vertebrae (known as C1 through C7), while the thoracic region consists of 12 vertebrae (known as T1 through T12). The cervical region extends generally from the base of the neck to the base of the skull, which is known as the occipital lobe. The thoracic region extends generally from the base of the neck to the base of the rib cage.

There are a variety of devices available to treat pain in portions of the body that include the cervical or thoracic regions of the spine. One such device is a neck brace, which could be made either of a soft foam rubber, a rigid material, or a combination thereof. A typical neck brace consists of thin foam, which is encased by a hard plastic shell that restricts head and neck movement after surgery on or near the cervical spine. A number of different single-site support devices are also available, including shoulder braces and clavicle straps made of soft, breathable foam and cotton material. While these devices can stabilize or immobilize certain parts of the body and prevent further injury, these devices have proven insufficient at alleviating and relieving pain in many individuals suffering from painful conditions in the neck, shoulders, and upper back. In addition, these prior art devices can cause headaches and discomfort for wearers, and thus may impart inferior remedial functionality, particularly for injuries that involve both the cervical and thoracic portions of the spine.

A variety of compression shirts are also currently available for use in athletic endeavors or for post-surgical treatment, but they do not include a compressive cervical collar, and have no means of providing compressive support to the cervical portion of the spine in combination with thoracic compressive support. In addition, while those compressive shirts may include means for tightening or loosening the compressive support, they lack a means to tighten or adjust the compressive support for regions of the body other than the thorax, such as the cervical portion of the spine. This means that these existing compression shirts are often ineffective or unable to be used to relieve suffering from neck, shoulder, and back pain for certain individuals.

Thus, there is no existing compression garment that provides combinatorial and continuous girded compressive support that encircles the wearer's body and extends from the base of the occipital lobe through the thoracic spine, to aid in recovery from surgery or a non-surgical injury, and to relieve joint and muscle pain in those regions of a wearer's body. Accordingly, there is a need for a resiliently flexible compression garment to provide girded support and treatment for both the cervical and thoracic regions of the body.

BRIEF SUMMARY OF THE INVENTION

The present invention comprises a resiliently flexible compression garment adapted to encircle both the thorax and cervical regions of the wearer's body, that further comprises a cervical collar and a fastening placket. The present invention is further directed to a gird compression garment made of bi-directional stretchable fabric that is adapted to extend from the base of the occipital lobe of a wearer to at least approximately the twelfth thoracic vertebra of a wearer. Preferably, the present invention comprises a plurality of resiliently flexible panels adapted to conform to the body of a wearer and extending from the wearer's shoulders to approximately the wearer's twelfth thoracic vertebra; a resiliently flexible cervical collar adapted to provide compressive support for the wearer's cervical vertebrae; and a fastening placket adapted to adjust the compressive force exerted by the garment on the wearer. The gird compression garment of the present invention is preferably adapted to encircle the wearer's body and extend from approximately the C1 vertebra of a wearer to the T12 vertebra of a wearer, so as to gird and support both the cervical and thoracic portions of the spine. Preferably, the cervical collar is integrally formed as part of the gird compression garment. More preferably, both the cervical collar as well as the panels adapted to conform to the body of a wearer are formed from a material that is bi-directionally stretchable, such as spandex or elastane. The bi-directionality of this material is advantageous because it allows for it to be oriented so as to provide effective, girded compressive support that extends from approximately the base of the occipital lobe of a wearer to approximately the twelfth thoracic vertebra of a wearer.

The object of the present invention is to provide relief from certain chronic upper body pain that is not fully treatable using prior art compression garments or other known treatment devices. By providing resiliently flexible, girded compression that is not limited to isolated portions of the upper body, but rather that extends throughout the entire cervical and thoracic regions, the embodiments of the present invention are adapted to provide remedial support for treatment of injuries and alleviation of pain. Furthermore, the embodiments of the present invention are adapted to provide for better joint coordination, more stable movements, and muscle relaxation for performance of daily activities.

The embodiments of the present invention are believed to be useful for the treatment of a variety of ailments, including neck radiculopathy, herniated discs in the upper back, dislocated joints, torn cartilage, torn muscles, torn ligaments, joint tendinitis, or joint arthritis, and in the prevention of injury recurrence. Furthermore, the embodiments of the present invention can be used to reduce and/or minimize pain in the cervical vertebrae, the thoracic vertebrae, the clavicle/collar bone, and the scapulars. In addition, the embodiments of the present invention can be particularly effective for treatment during the remodeling phase of muscle or joint recovery, i.e., after the injury phase, the acute/inflammatory phase, and the repair/regeneration phase have been completed. In this way, the embodiments of the present invention can aid in the rehabilitation of injuries and can promote comfort for a wearer.

DETAILED DESCRIPTION OF THE INVENTION

Figure 1:
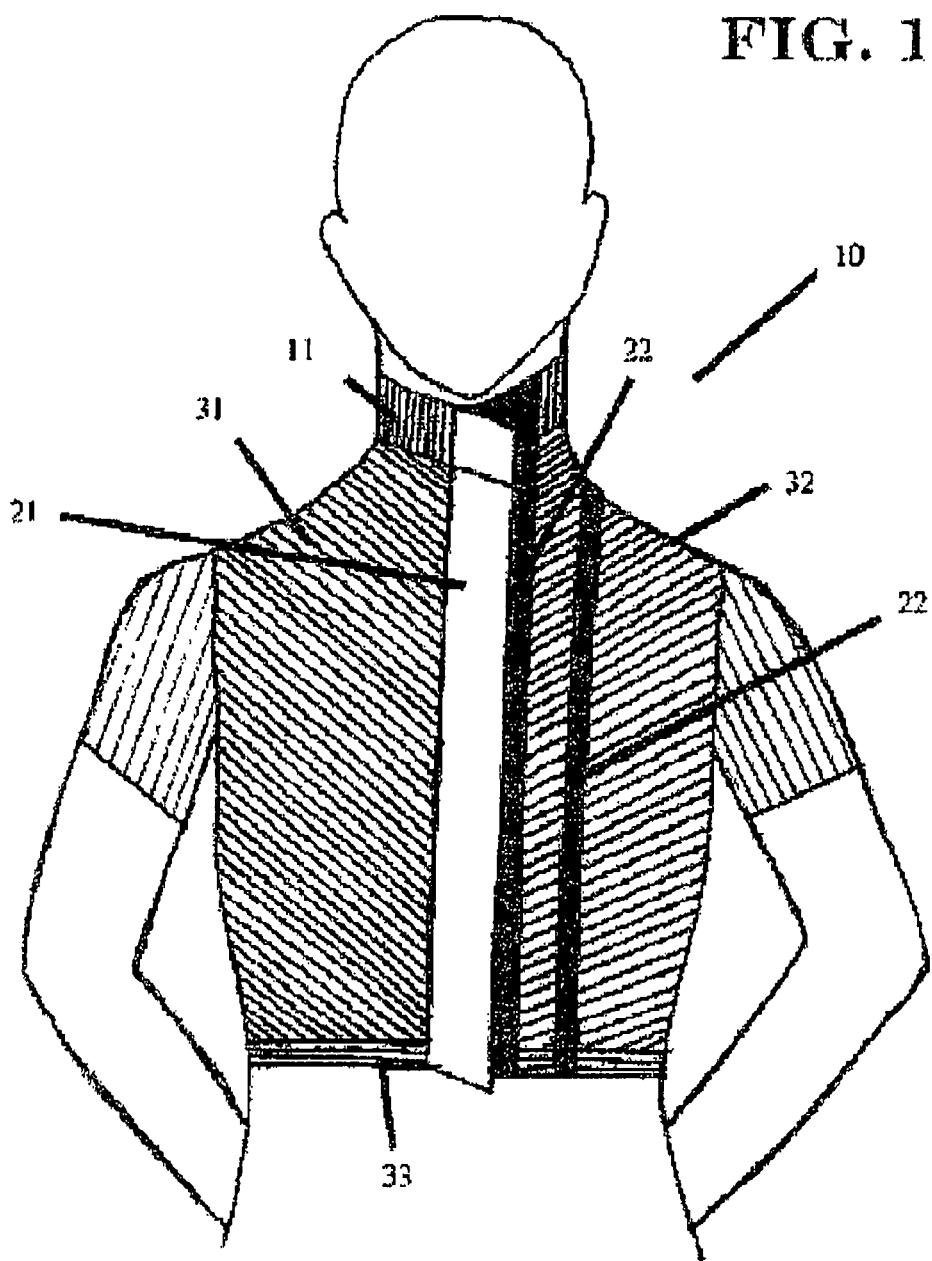
FIG. 1 is a front perspective of a gird compression garment with a cervical collar for a male user according to the present invention.

FIG. 1 illustrates the front view of an exemplary embodiment of a gird compression garment with cervical collar for a male user. The garment 10 of FIG. 1 comprises a right-side panel 31, which is adapted to conform to the right-hand side of a male wearer's thorax, and a left-side panel 32, which is adapted to conform to the left-hand side of a male wearer's thorax. The garment 10 of FIG. 1 further comprises a resiliently flexible cervical collar 11 adapted to encircle and conform to the anterior and posterior regions of a wearer's neck, so as to provide compressive support to the cervical vertebrae C1 through C7, for instance. In this preferred embodiment, the cervical collar 11 is integrally formed as part of the garment 10.

The garment 10 of FIG. 1 further comprises a fastening placket 21. Preferably, the fastening placket 21 is adapted to extend from the anterior portion of the wearer's neck to the base of the wearer's rib cage or to the anterior portion of the wearer's thorax (i.e., the wearer's sternum). Preferably, the fastening placket 21 is at least approximately 10 inches in length, and at least approximately 4 inches in width. The fastening placket 21 of this embodiment is further adapted to allow for the adjustment of the compressive force exerted by the garment 10 on the body of the wearer. The fastening placket 21 preferably includes a fastening strip that can be attached to one or more complementary fastening strips 22 located on a panel 31 or 32 of the garment 10. Multiple complementary fastening strips can be included on a panel of garment 10 to allow for the fastening placket 21 to be joined to a garment panel in varying positions (for varying the compressive force exerted). In the embodiment depicted in FIG. 1, the underside of the fastening placket 21 is adapted to be fastened to either of the fastening strips 22, which are spaced apart from one another. Those complementary fastening strips 22 may be integrally sewn into the panel 31 or 32. Preferably, the complementary fastening strip 22 is adapted to extend approximately the entire length of the fastening placket to ensure a strong, complementary connection. More preferably, the fastening placket 21 and complementary fastening strips 22 comprise VELCRO® brand hook-and-loop or touch fasteners.

In a preferred embodiment, the fastening placket 21 is sewn into the garment 10, such that the lining or backing of the fastening placket 21 is exposed on the front portion of the garment 10. More preferably, the fastening placket 21 is sewn into the right-side panel 31, such that the backing or liner of the fastening placket 21 is covered by the same resiliently flexible material as the panels 31 and 32.

The garment 10 further comprises a thoracic base strip 33. This thoracic base strip 33 is adapted to encircle the lower thorax of a wearer, at a location approximately at the wearer's twelfth thoracic vertebra, known as T12. Within the scope of the present invention are variations in the length of the garment 10, so that it may extend, for instance, to just the eleventh or tenth thoracic vertebra of a wearer, or as far as the first or second vertebra of the lumbar region.

The garment 10, including the panels 31, 32, the cervical collar 11, and the thoracic base strip 33, are preferably made from a resiliently flexible material that is bi-directionally stretchable. More preferably, all of those portions of the garment 10 are made from the same resiliently flexible, bi-directionally stretchable material. More preferably, the resiliently flexible material is more stretchable in a first direction than it is in a second, perpendicular direction. For instance, bi-directionally stretchable resiliently flexible materials that are well-suited to the present invention include spandex, polyester, or elastane that is approximately four times as stretchable in a first direction than it is a second, perpendicular direction.

Preferably, the bi-directionally stretchable resiliently flexible material is oriented so that the more stretchable axis of the material is oriented diagonally with respect to the median or sagittal plane of the wearer's body. This orientation is illustrated in FIG. 1 by the parallel, striated lines that form an angle with respect to the median plane (which is parallel to the fastening placket 21). This diagonal orientation is believed to provide for superior compressive support as compared to prior art garments because it better mimics and enhances certain compressive forces of the thoracic musculature.

Figure 2:
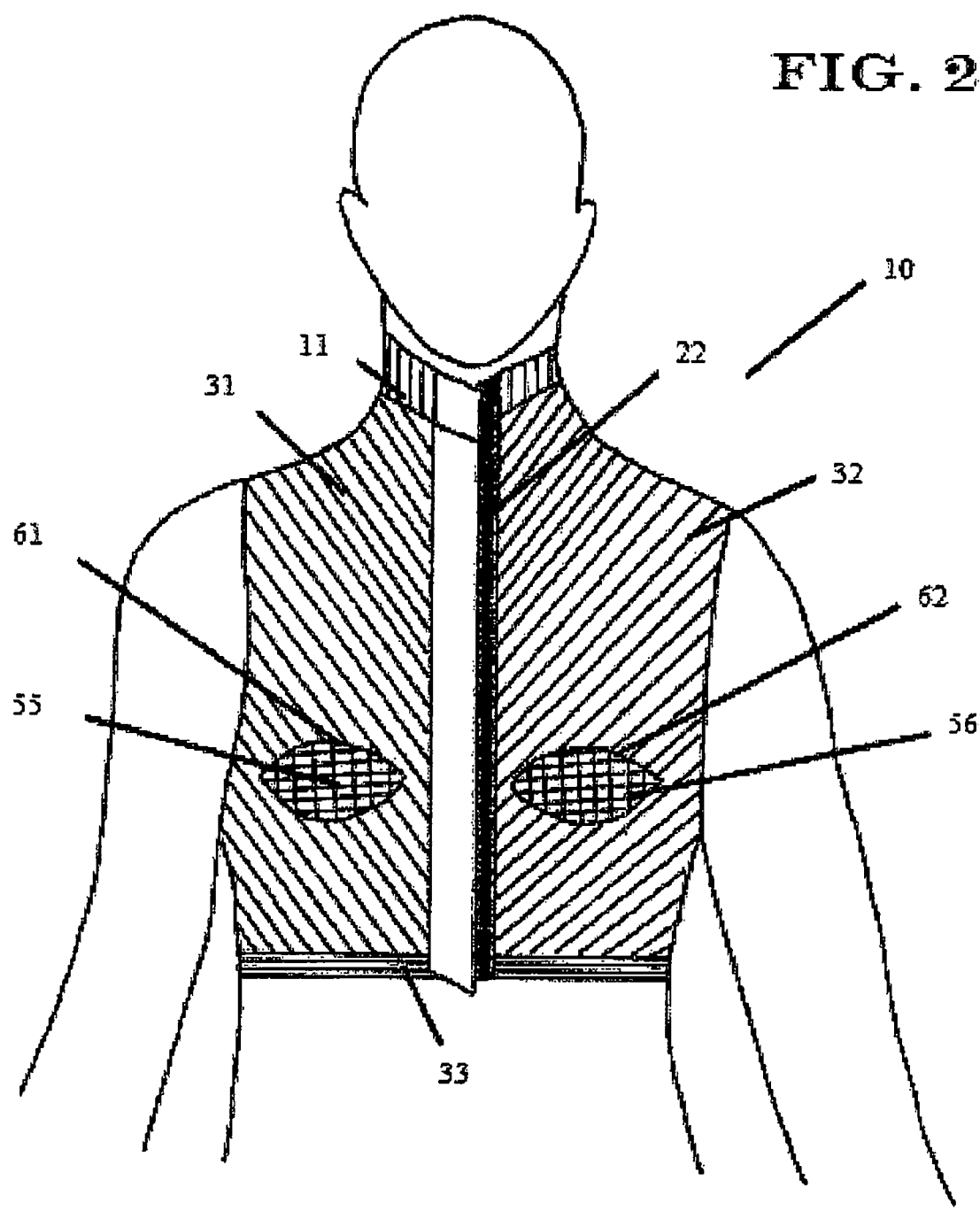
FIG. 2 is a front perspective of a gird compression garment with a cervical collar for a female user according to the present invention.

FIG. 2 illustrates the front view of an exemplary embodiment of a gird compression garment. 10 with cervical collar 11 for a female user. This embodiment is generally similar to that depicted in FIG. 1, except that the right-side panel 31 includes a cut-out 61 that is adapted to accommodate a breast panel. 55, and the left-side panel 32 also includes a cut-out 62 that is adapted to accommodate a breast panel 56. These additional panels 55 and 56 can preferably be included in the design of the garment 10 to provide greater comfort for a female wearer. Because of the strong compressive forces exerted by the garment 10, a female wearer can experience discomfort if the panels are not adapted to provide additional space to accommodate the breasts. The breast panels 55 and 56 are preferably made of mesh fabric or netting, and are preferably the shape of a prolate spheroid, as shown in FIG. 2, or an oval shape, as shown in breast panels 57 and 58 in FIG. 4, FIG. 4 also depicts a cut-out 63 and a cut-out 64 which are adapted to accommodate the aforementioned breast panels 57 and 58 respectively.

Figure 3:
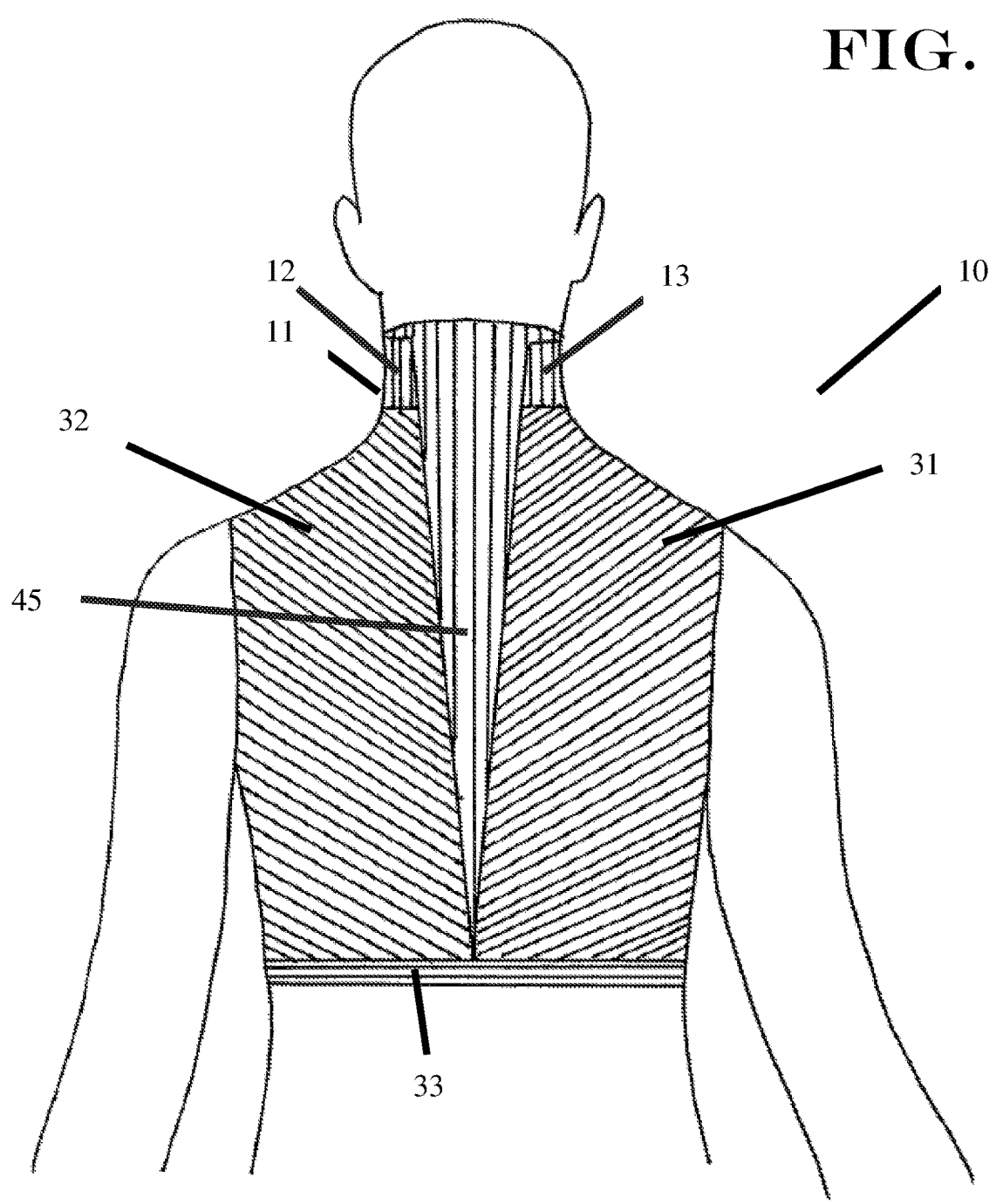
FIG. 3 is a rear perspective of a gird compression garment with a cervical collar for a male or female user according to the present invention.

FIG. 3 illustrates the rear view of an exemplary embodiment of a gird compression garment 10 with cervical collar 11. This rear view applies to embodiments of the present invention for both male and female wearers. In other words, this rear view is the same for both the embodiment adapted for a male wearer depicted in FIG. 1 and the embodiment adapted for a female wearer depicted in FIG. 2.

The rear view of this embodiment includes a yoke panel 45. Preferably, the right and left panels 31 and 32, respectively, are sewn into opposite sides of the yoke panel 45. More preferably, the yoke panel 45 is V-shaped with an acute angle, as shown in FIG. 3. The yoke panel 45 can preferably extend up to the base of the occipital lobe of a wearer, and is preferably made from the same bi-directionally stretchable, resiliently flexible material as the other portions of the garment 10, e.g., spandex or elastane. Preferably, the cervical collar 11 is rounded at its upper-most portion, as shown in FIG. 3.

In this embodiment, the cervical collar 11 is preferably formed by coupling together three elements: the upper portion of a yoke panel 45, a left-side collar portion 12, and a right-side collar portion 13, as illustrated in FIG. 3. The resiliently flexible material that comprises the yoke panel 45 is preferably oriented so that the more stretchable axis of the material is oriented parallel to the median or sagittal plane of the wearer's body, and along the spinal column of the wearer. This orientation is shown by the vertical striated lines depicted in the interior of the yoke panel 45 in FIG. 3. It is believed that this particular orientation and the fact that the yoke panel 45 is adapted to extend from the base of the occipital lobe of the wearer to the top of the thoracic base strip 33 are collectively effective at reducing pain in the upper back and neck of a wearer, while advantageously allowing the wearer to bend and flex the back and neck with continuous support from the garment 10.

Figure 4:
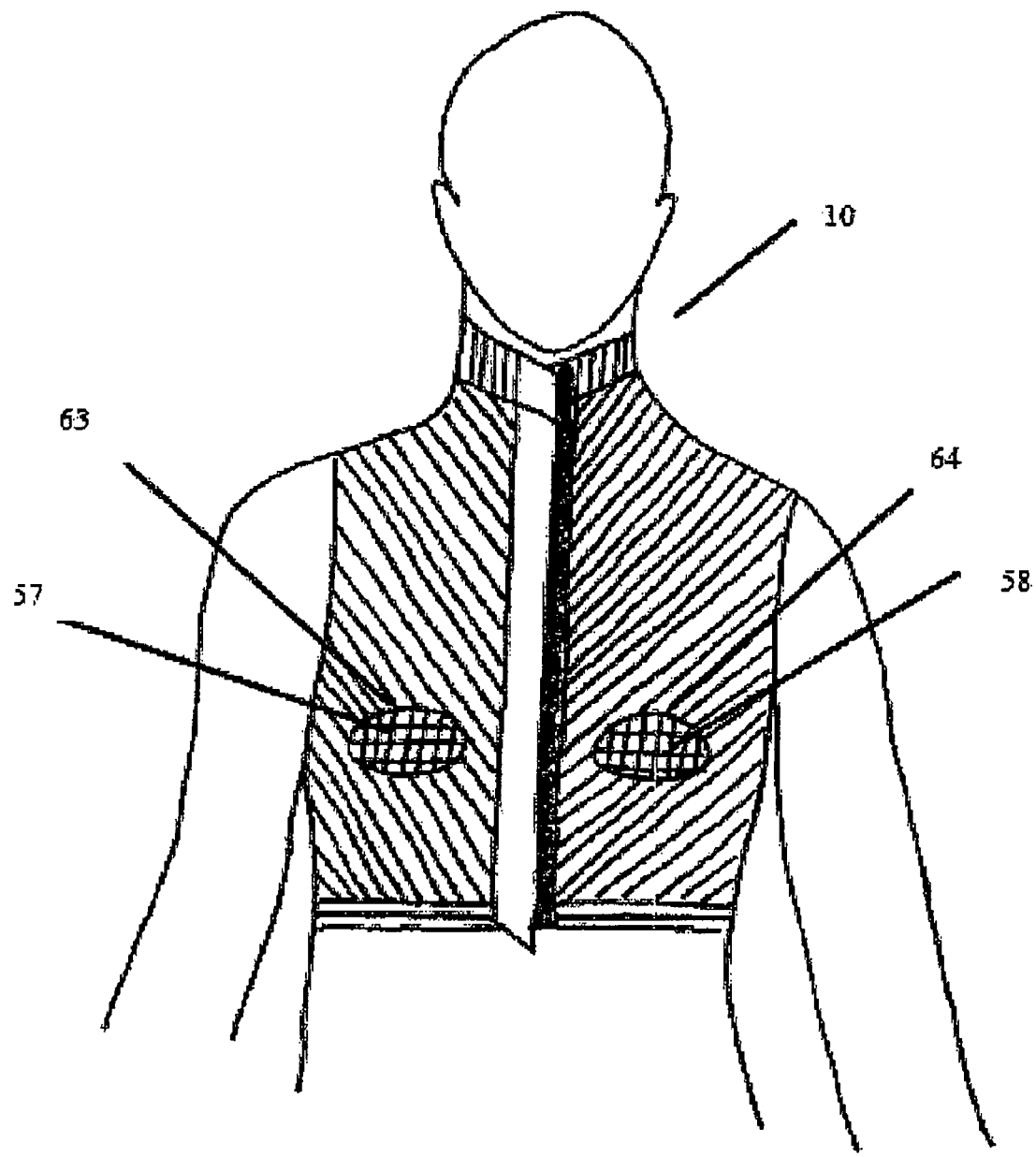
FIG. 4 is a front perspective of an embodiment of a gird compression garment with a cervical collar for a female user according to the present invention, illustrating the use of cutouts shaped as ovals.

The depicted garment 10 in FIGS. 2-4 is sleeveless; however, other embodiments of the present invention, as shown for instance in FIG. 1, comprise sleeves of varying lengths, including full sleeves extending to at least approximately the location of the wearer's wrists, three-quarter length sleeves, and half sleeves.

Although the preferred embodiment of the invention has been described in detail for purposes of illustration, various modifications may be made without departing from the scope and spirit of the invention.

The invention claimed is:

1. A gird compression garment, comprising:
a plurality of resiliency flexible panels adapted to conform to a body of a wearer, said plurality of resiliently flexible panels made from a bi-directionally stretchable material that is more stretchable in a first direction than it is in a second, perpendicular direction, and said plurality of resiliently flexible panels oriented so that a more stretchable axis of the bi-directionally stretchable material is diagonal to a vertical plane of the body of the wearer;
wherein said plurality of resiliently flexible panels comprise a right-side panel adapted: to compressively gird a right-hand side of the body of the wearer and a left-side panel adapted to compressively gird a left-hand side of the body of the wearer,
wherein said right-side panel and said left-side panel are joined by a vertically oriented yoke panel on a rear side of said garment, wherein said vertically oriented yoke panel is made from a bi-directionally stretchable material that is more stretchable in a first direction than it is in a second, perpendicular direction, and said vertically oriented yoke panel oriented so that the more stretchable axis of the bi-directionally stretchable material is parallel to a sagittal plane of the body of the wearer;
a resiliently flexible cervical collar adapted to provide compressive support for the wearer, wherein said resiliently flexible cervical collar is formed by coupling together a left-side collar portion, a right-side collar portion, and an upper portion of said vertically oriented yoke panel; and
a fastening placket adapted to adjust a compressive force exerted by said garment on the wearer.

2. The gird compression garment of claim 1, wherein said garment further comprises a resiliently flexible sleeve adapted to compressively gird the right arm of the wearer and a resiliently flexible sleeve adapted to compressively gird the left arm of the wearer.

3. The gird compression garment of claim 2, wherein each resiliently flexible sleeve is made of a bi-directionally stretchable material.

4. The gird compression garment of claim 3, wherein each resiliently flexible sleeve is made of spandex.

5. The gird compression garment of claim 1, wherein said resiliently flexible cervical collar is integrally formed with said plurality of resiliently flexible panels.

6. The gird compression garment of claim 5, wherein said plurality of resiliently flexible panels and said resiliently, flexible cervical collar are made of spandex.

7. The gird compression garment of claim 2, wherein said vertically oriented yoke panel comprises spandex.

8. The gird compression garment of claim 1, wherein said plurality of resiliently flexible panels each includes a cutout shaped as a prolate spheroid.

9. The gird compression garment of claim 8, wherein each said cutout is covered with a mesh fabric sewn into said garment.

10. The gird compression garment of claim 1, wherein each panel of said plurality of resiliently flexible panels includes a cutout shaped as an oval.

11. The gird compression garment of claim 10, wherein each said cutout is covered with a mesh fabric sewn into said garment.

12. The gird compression garment of claim 1, wherein said garment further comprises a resiliently flexible thoracic base strip adapted to gird the body of the wearer at a lowermost point of said plurality of resiliently flexible panels.

13. The gird compression garment of claim 1, wherein at least one of said plurality of resiliently flexible panels comprises a fastening strip that is complementary to said fastening placket.

14. The gird compression garment of claim 1, wherein said garment is sleeveless.

* * * * *